(12) United States Patent
Kravchenko et al.

(10) Patent No.: US 10,251,825 B2
(45) Date of Patent: Apr. 9, 2019

(54) COMPOSITION WITH INSECT REPELLENT ACTIVITY

(71) Applicants: Iryna Kravchenko, Santa Clara, CA (US); Mariia Nesterkina, Santa Clara, CA (US); Sergiy Lozovsky, Santa Clara, CA (US)

(72) Inventors: Iryna Kravchenko, Santa Clara, CA (US); Mariia Nesterkina, Santa Clara, CA (US); Sergiy Lozovsky, Santa Clara, CA (US)

( * ) Notice: Subject to any disclaimer, the term of this patent is extended or adjusted under 35 U.S.C. 154(b) by 0 days.

(21) Appl. No.: 15/662,436

(22) Filed: Jul. 28, 2017

(65) Prior Publication Data

US 2018/0028422 A1 Feb. 1, 2018

Related U.S. Application Data

(60) Provisional application No. 62/368,169, filed on Jul. 29, 2016.

(51) Int. Cl.
| | | |
|---|---|---|
| *A61K 8/37* | (2006.01) |
| *A61K 8/34* | (2006.01) |
| *A61K 8/46* | (2006.01) |
| *A01N 25/32* | (2006.01) |
| *A61K 8/92* | (2006.01) |
| *A61K 9/00* | (2006.01) |
| *A61Q 17/02* | (2006.01) |
| *A61K 8/42* | (2006.01) |
| *A61K 8/55* | (2006.01) |
| *A01N 37/44* | (2006.01) |
| *A61K 8/44* | (2006.01) |
| *A61K 9/06* | (2006.01) |
| *A61K 47/44* | (2017.01) |
| *A01N 31/08* | (2006.01) |

(52) U.S. Cl.
CPC ............... *A61K 8/37* (2013.01); *A01N 25/32* (2013.01); *A01N 31/08* (2013.01); *A01N 37/44* (2013.01); *A61K 8/34* (2013.01); *A61K 8/347* (2013.01); *A61K 8/42* (2013.01); *A61K 8/44* (2013.01); *A61K 8/466* (2013.01); *A61K 8/55* (2013.01); *A61K 8/922* (2013.01); *A61K 9/0014* (2013.01); *A61K 9/06* (2013.01); *A61K 47/44* (2013.01); *A61Q 17/02* (2013.01); *A61K 2300/00* (2013.01)

(58) Field of Classification Search
None
See application file for complete search history.

(56) References Cited

U.S. PATENT DOCUMENTS

| 5,227,163 A * | 7/1993 | Eini ..................... A01N 27/00 514/546 |
| 2015/0197484 A1* | 7/2015 | Stinchcomb ......... A61K 9/0021 424/642 |
| 2018/0008717 A1* | 1/2018 | Kravchenko ........ A61K 47/542 |

OTHER PUBLICATIONS

Urabe, D. "Convergent Strategies in Total Syntheses of Complex Terpenoids" Chemical Reviews, 2015, 115, 9207-9231.*

* cited by examiner

*Primary Examiner* — Mina Haghighatian
*Assistant Examiner* — Erin E Hirt

(57) ABSTRACT

A composition comprising a compound having a Formula I:

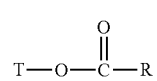

wherein T is derivative of a terpene and R is a derivative of a neurotransmitter amino acid. Pharmaceutical formulations for topical use as insect repellents including the terpenes and terpene esters in form of the pharmaceutically acceptable salt or base are provided. A process for preparing the composition and the formulations are also provided.

6 Claims, No Drawings

COMPOSITION WITH INSECT REPELLENT ACTIVITY

CROSS-REFERENCE TO RELATED APPLICATIONS

The present Utility patent application claims priority benefit of the U.S. provisional application for patent Ser. No. 62/368,169 entitled "TERPENOID INSECT REPELLENT COMPOSITIONS" filed 29 Jul. 2016 under 35 U.S.C. 119(e). The contents of this related provisional application are incorporated herein by reference for all purposes to the extent that such subject matter is not inconsistent herewith or limiting hereof.

INCORPORATION BY REFERENCE OF SEQUENCE LISTING PROVIDED AS A TEXT FILE

Not applicable.

FEDERALLY SPONSORED RESEARCH OR DEVELOPMENT

Not applicable.

REFERENCE TO SEQUENCE LISTING, A TABLE, OR A COMPUTER LISTING APPENDIX

Not applicable.

COPYRIGHT NOTICE

A portion of the disclosure of this patent document contains material that is subject to copyright protection by the author thereof. The copyright owner has no objection to the facsimile reproduction by anyone of the patent document or patent disclosure for the purposes of referencing as patent prior art, as it appears in the Patent and Trademark Office, patent file or records, but otherwise reserves all copyright rights whatsoever.

BACKGROUND OF THE RELEVANT PRIOR ART

One or more embodiments of the invention generally relate to compositions having insect repellent effect. More particularly, certain embodiments of the invention relates to compositions that include esters based on terpenoids and neurotransmitter amino acids having insect repellent effect.

The following background information may present examples of specific aspects of the prior art (e.g., without limitation, approaches, facts, or common wisdom) that, while expected to be helpful to further educate the reader as to additional aspects of the prior art, is not to be construed as limiting the present invention, or any embodiments thereof, to anything stated or implied therein or inferred thereupon. Arthropods are typically considered to be dangerous vectors of deadly pathogens and parasites, and are believed to be a key threat to millions of people around the world. They are believed to transfer malaria pathogens, yellow fever, dengue fever, West Nile, Chikungunya virus, filariasis, Zika virus and others. Research is ongoing in the pharmaceutical industry for new compositions having insect repellent effect. The following is an example of a specific aspect in the prior art that, while expected to be helpful to further educate the reader as to additional aspects of the prior art, is not to be construed as limiting the present invention, or any embodiments thereof, to anything stated or implied therein or inferred thereupon. By way of educational background, another aspect of the prior art generally useful to be aware of is that monoterpenoids have been developed and studied as insecticides for many years, however, their mode of action is not yet very clear. Monoterpenoids may act on various targets in insects, especially on the nervous system, including γ-aminobutyric acid (GABA)-gated chloride channels, octopamine receptors, tyramine receptors, acetylcholine esterase, nicotinic acetylcholine receptors (nAChR), sodium channels, and possibly other methods. The different monoterpenoids are believed to bind to ionotropic GABA receptors in insects. Thymol, linalool, menthol, camphor, carvone, borneol, and other monoterpenoids were shown to be positive allosteric modulators of insects' GABA receptors. G-protein-coupled receptors in insects including octopamine receptors and tyramine receptors are also believed to be candidate targets for monoterpenoid insecticides. Carvacrol, alpha-terpineol, pulegone, eugenol, and about twenty other monoterpenoids were demonstrated to have binding activities at an octopamine receptor from American cockroach with high sensitivities. They were either antagonists or agonists of the octopamine receptor.

In view of the foregoing, it is clear that these traditional techniques are not perfect and leave room for more optimal approaches.

DETAILED DESCRIPTION OF SOME EMBODIMENTS

The present invention is best understood by reference to the examples and description set forth herein.

Embodiments of the invention are discussed below with reference to the Figures. However, those skilled in the art will readily appreciate that the detailed description given herein with respect to these figures is for explanatory purposes as the invention extends beyond these limited embodiments. For example, it should be appreciated that those skilled in the art will, in light of the teachings of the present invention, recognize a multiplicity of alternate and suitable approaches, depending upon the needs of the particular application, to implement the functionality of any given detail described herein, beyond the particular implementation choices in the following embodiments described and shown. That is, there are modifications and variations of the invention that are too numerous to be listed but that all fit within the scope of the invention. Also, singular words should be read as plural and vice versa and masculine as feminine and vice versa, where appropriate, and alternative embodiments do not necessarily imply that the two are mutually exclusive.

It is to be further understood that the present invention is not limited to the particular methodology, compounds, materials, manufacturing techniques, uses, and applications, described herein, as these may vary. It is also to be understood that the terminology used herein is used for the purpose of describing particular embodiments only, and is not intended to limit the scope of the present invention. It must be noted that as used herein and in the appended claims, the singular forms "a," "an," and "the" include the plural reference unless the context clearly dictates otherwise. Thus, for example, a reference to "an element" is a reference to one or more elements and includes equivalents thereof known to those skilled in the art. Similarly, for another example, a reference to "a step" or "a means" is a reference to one or more steps or means and may include sub-steps and subservient means. All conjunctions used are to be understood in the most inclusive sense possible. Thus, the word "or" should be understood as having the definition of a logical "or" rather than that of a logical "exclusive or" unless the context clearly necessitates otherwise. Structures described herein are to be understood also to refer to functional equivalents of such structures. Language that may be construed to express approximation should be so understood unless the context clearly dictates otherwise.

All words of approximation as used in the present disclosure and claims should be construed to mean "approximate," rather than "perfect," and may accordingly be employed as a meaningful modifier to any other word, specified parameter, quantity, quality, or concept. Words of approximation, include, yet are not limited to terms such as "substantial", "nearly", "almost", "about", "generally", "largely", "essentially", "closely approximate", etc.

As will be established in some detail below, it is well settle law, as early as 1939, that words of approximation are not indefinite in the claims even when such limits are not defined or specified in the specification.

For example, see *Ex parte Mallory*, 52 USPQ 297, 297 (Pat. Off. Bd. App. 1941) where the court said "The examiner has held that most of the claims are inaccurate because apparently the laminar film will not be entirely eliminated. The claims specify that the film is "substantially" eliminated and for the intended purpose, it is believed that the slight portion of the film which may remain is negligible. We are of the view, therefore, that the claims may be regarded as sufficiently accurate."

Note that claims need only "reasonably apprise those skilled in the art" as to their scope to satisfy the definiteness requirement. See *Energy Absorption Sys., Inc.* v. *Roadway Safety Servs., Inc.*, Civ. App. 96-1264, slip op. at 10 (Fed. Cir. Jul. 3, 1997) (unpublished) *Hybridtech* v. *Monoclonal Antibodies, Inc.*, 802 F.2d 1367, 1385, 231 USPQ 81, 94 (Fed. Cir. 1986), cert. denied, 480 U.S. 947 (1987). In addition, the use of modifiers in the claim, like "generally" and "substantial," does not by itself render the claims indefinite. See *Seattle Box Co.* v. *Industrial Crating & Packing, Inc.*, 731 F.2d 818, 828-29, 221 USPQ 568, 575-76 (Fed. Cir. 1984).

Moreover, the ordinary and customary meaning of terms like "substantially" includes "reasonably close to: nearly, almost, about", connoting a term of approximation. See In re *Frye*, Appeal No. 2009-006013, 94 USPQ2d 1072, 1077, 2010 WL 889747 (B.P.A.I. 2010) Depending on its usage, the word "substantially" can denote either language of approximation or language of magnitude. *Deering Precision Instruments, L.L.C.* v. *Vector Distribution Sys., Inc.*, 347 F.3d 1314, 1323 (Fed. Cir. 2003) (recognizing the "dual ordinary meaning of th[e] term ["substantially"] as connoting a term of approximation or a term of magnitude"). Here, when referring to the "substantially halfway" limitation, the Specification uses the word "approximately" as a substitute for the word "substantially" (Fact 4). (Fact 4). The ordinary meaning of "substantially halfway" is thus reasonably close to or nearly at the midpoint between the forwardmost point of the upper or outsole and the rearwardmost point of the upper or outsole.

Similarly, the term 'substantially' is well recognize in case law to have the dual ordinary meaning of connoting a term of approximation or a term of magnitude. See *Dana Corp.* v. *American Axle & Manufacturing, Inc.*, Civ. App. 04-1116, 2004 U.S. App. LEXIS 18265, *13-14 (Fed. Cir. Aug. 27, 2004) (unpublished). The term "substantially" is commonly used by claim drafters to indicate approximation. See *Cordis Corp.* v. *Medtronic AVE Inc.*, 339 F.3d 1352, 1360 (Fed. Cir. 2003) ("The patents do not set out any numerical standard by which to determine whether the thickness of the wall surface is 'substantially uniform.' The term 'substantially,' as used in this context, denotes approximation. Thus, the walls must be of largely or approximately uniform thickness."); see also *Deering Precision Instruments, LLC* v. *Vector Distribution Sys., Inc.*, 347 F.3d 1314, 1322 (Fed. Cir. 2003); *Epcon Gas Sys., Inc.* v. *Bauer Compressors, Inc.*, 279 F.3d 1022, 1031 (Fed. Cir. 2002). We find that the term "substantially" was used in just such a manner in the claims of the patents-in-suit: "substantially uniform wall thickness" denotes a wall thickness with approximate uniformity.

It should also be noted that such words of approximation as contemplated in the foregoing clearly limits the scope of claims such as saying 'generally parallel' such that the adverb 'generally' does not broaden the meaning of parallel. Accordingly, it is well settled that such words of approximation as contemplated in the foregoing (e.g., like the phrase 'generally parallel') envisions some amount of deviation from perfection (e.g., not exactly parallel), and that such words of approximation as contemplated in the foregoing are descriptive terms commonly used in patent claims to avoid a strict numerical boundary to the specified parameter. To the extent that the plain language of the claims relying on such words of approximation as contemplated in the foregoing are clear and uncontradicted by anything in the written description herein or the figures thereof, it is improper to rely upon the present written description, the figures, or the prosecution history to add limitations to any of the claim of the present invention with respect to such words of approximation as contemplated in the foregoing. That is, under such circumstances, relying on the written description and prosecution history to reject the ordinary and customary meanings of the words themselves is impermissible. See, for example, *Liquid Dynamics Corp.* v. *Vaughan Co.*, 355 F.3d 1361, 69 USPQ2d 1595, 1600-01 (Fed. Cir. 2004). The plain language of phrase 2 requires a "substantial helical flow." The term "substantial" is a meaningful modifier implying "approximate," rather than "perfect." In *Cordis Corp.* v. *Medtronic AVE, Inc.*, 339 F.3d 1352, 1361 (Fed. Cir. 2003), the district court imposed a precise numeric constraint on the term "substantially uniform thickness." We noted that the proper interpretation of this term was "of largely or approximately uniform thickness" unless something in the prosecution history imposed the "clear and unmistakable disclaimer" needed for narrowing beyond this simple-language interpretation. Id. In *Anchor Wall Systems* v. *Rockwood Retaining Walls, Inc.*, 340 F.3d 1298, 1311 (Fed. Cir. 2003)" Id. at 1311. Similarly, the plain language of Claim 1 requires neither a perfectly helical flow nor a flow that returns precisely to the center after one rotation (a limitation that arises only as a logical consequence of requiring a perfectly helical flow).

The reader should appreciate that case law generally recognizes a dual ordinary meaning of such words of approximation, as contemplated in the foregoing, as connoting a term of approximation or a term of magnitude; e.g., see *Deering Precision Instruments, L.L.C.* v. *Vector Distrib. Sys., Inc.*, 347 F.3d 1314, 68 USPQ2d 1716, 1721 (Fed. Cir. 2003), cert. denied, 124 S. Ct. 1426 (2004) where the court was asked to construe the meaning of the term "substantially" in a patent claim. Also see *Epcon*, 279 F.3d at 1031 ("The phrase 'substantially constant' denotes language of approximation, while the phrase 'substantially below' signifies language of magnitude, i.e., not insubstantial."). Also, see, e.g., *Epcon Gas Sys., Inc.* v. *Bauer Compressors, Inc.*, 279 F.3d 1022 (Fed. Cir. 2002) (construing the terms "substantially constant" and "substantially below"); *Zodiac Pool Care, Inc.* v. *Hoffinger Indus., Inc.*, 206 F.3d 1408 (Fed. Cir. 2000) (construing the term "substantially inward"); *York Prods., Inc.* v. *Cent. Tractor Farm & Family Ctr.*, 99 F.3d 1568 (Fed. Cir. 1996) (construing the term "substantially the entire height thereof"); *Tex. Instruments Inc.* v. *Cypress Semiconductor Corp.*, 90 F.3d 1558 (Fed. Cir. 1996) (construing the term "substantially in the common plane"). In conducting their analysis, the court instructed to begin with the ordinary meaning of the claim terms to one of ordinary skill in the art. *Prima Tek*, 318 F.3d at 1148. Reference to dictionaries and our cases indicates that the term "substantially" has numerous ordinary meanings. As the district court stated, "substantially" can mean "significantly" or "considerably." The term "substantially" can also mean "largely" or "essentially." Webster's New 20th Century Dictionary 1817 (1983).

Words of approximation, as contemplated in the foregoing, may also be used in phrases establishing approximate ranges or limits, where the end points are inclusive and approximate, not perfect; e.g., see *AK Steel Corp.* v. *Sollac*, 344 F.3d 1234, 68 USPQ2d 1280, 1285 (Fed. Cir. 2003) where it where the court said [W]e conclude that the ordinary meaning of the phrase "up to about 10%" includes the "about 10%" endpoint. As pointed out by AK Steel, when an object of the preposition "up to" is nonnumeric, the most natural meaning is to exclude the object (e.g., painting the wall up to the door). On the other hand, as pointed out by Sollac, when the object is a numerical limit, the normal meaning is to include that upper numerical limit (e.g., counting up to ten, seating capacity for up to seven passengers). Because we have here a numerical limit—"about 10%"—the ordinary meaning is that that endpoint is included.

In the present specification and claims, a goal of employment of such words of approximation, as contemplated in the foregoing, is to avoid a strict numerical boundary to the modified specified parameter, as sanctioned by *Pall Corp.* v. *Micron Separations, Inc.*, 66 F.3d 1211, 1217, 36 USPQ2d 1225, 1229 (Fed. Cir. 1995) where it states "It is well established that when the term "substantially" serves reasonably to describe the subject matter so that its scope would be understood by persons in the field of the invention, and to distinguish the claimed subject matter from the prior art, it is not indefinite." Likewise see *Verve LLC* v. *Crane Cams Inc.*, 311 F.3d 1116, 65 USPQ2d 1051, 1054 (Fed. Cir. 2002). Expressions such as "substantially" are used in patent documents when warranted by the nature of the invention, in order to accommodate the minor variations that may be appropriate to secure the invention. Such usage may well satisfy the charge to "particularly point out and distinctly claim" the invention, 35 U.S.C. § 112, and indeed may be necessary in order to provide the inventor with the benefit of his invention. In *Andrew Corp.* v. *Gabriel Elecs. Inc.*, 847 F.2d 819, 821-22, 6 USPQ2d 2010, 2013 (Fed. Cir. 1988) the court explained that usages such as "substantially equal" and "closely approximate" may serve to describe the invention with precision appropriate to the technology and without intruding on the prior art. The court again explained in *Ecolab Inc.* v. *Envirochem, Inc.*, 264 F.3d 1358, 1367, 60 USPQ2d 1173, 1179 (Fed. Cir. 2001) that "like the term 'about,' the term 'substantially' is a descriptive term commonly used in patent claims to 'avoid a strict numerical boundary to the specified parameter, see *Ecolab Inc.* v. *Envirochem Inc.*, 264 F.3d 1358, 60 USPQ2d 1173, 1179 (Fed. Cir. 2001) where the court found that the use of the term "substantially" to modify the term "uniform" does not render this phrase so unclear such that there is no means by which to ascertain the claim scope.

Similarly, other courts have noted that like the term "about," the term "substantially" is a descriptive term commonly used in patent claims to "avoid a strict numerical boundary to the specified parameter."; e.g., see *Pall Corp.* v. *Micron Seps.*, 66 F.3d 1211, 1217, 36 USPQ2d 1225, 1229 (Fed. Cir. 1995); see, e.g., *Andrew Corp.* v. *Gabriel Elecs. Inc.*, 847 F.2d 819, 821-22, 6 USPQ2d 2010, 2013 (Fed. Cir. 1988) (noting that terms such as "approach each other," "close to," "substantially equal," and "closely approximate" are ubiquitously used in patent claims and that such usages, when serving reasonably to describe the claimed subject matter to those of skill in the field of the invention, and to distinguish the claimed subject matter from the prior art, have been accepted in patent examination and upheld by the courts). In this case, "substantially" avoids the strict 100% nonuniformity boundary.

Indeed, the foregoing sanctioning of such words of approximation, as contemplated in the foregoing, has been established as early as 1939, see *Ex parte Mallory*, 52 USPQ 297, 297 (Pat. Off. Bd. App. 1941) where, for example, the court said "the claims specify that the film is "substantially" eliminated and for the intended purpose, it is believed that the slight portion of the film which may remain is negligible. We are of the view, therefore, that the claims may be regarded as sufficiently accurate." Similarly, In re *Hutchison*, 104 F.2d 829, 42 USPQ 90, 93 (C.C.P.A. 1939) the court said "It is realized that "substantial distance" is a relative and somewhat indefinite term, or phrase, but terms and phrases of this character are not uncommon in patents in cases where, according to the art involved, the meaning can be determined with reasonable clearness."

Hence, for at least the forgoing reason, Applicants submit that it is improper for any examiner to hold as indefinite any claims of the present patent that employ any words of approximation.

Unless defined otherwise, all technical and scientific terms used herein have the same meanings as commonly understood by one of ordinary skill in the art to which this invention belongs. Preferred methods, techniques, devices, and materials are described, although any methods, techniques, devices, or materials similar or equivalent to those described herein may be used in the practice or testing of the present invention. Structures described herein are to be understood also to refer to functional equivalents of such structures. The present invention will be described in detail below with reference to embodiments thereof as illustrated in the accompanying drawings.

References to a "device," an "apparatus," a "system," etc., in the preamble of a claim should be construed broadly to mean "any structure meeting the claim terms" exempt for any specific structure(s)/type(s) that has/(have) been explicitly disavowed or excluded or admitted/implied as prior art in the present specification or incapable of enabling an object/aspect/goal of the invention. Furthermore, where the present specification discloses an object, aspect, function, goal, result, or advantage of the invention that a specific prior art structure and/or method step is similarly capable of performing yet in a very different way, the present invention disclosure is intended to and shall also implicitly include and cover additional corresponding alternative embodiments that are otherwise identical to that explicitly disclosed except that they exclude such prior art structure(s)/step(s), and shall accordingly be deemed as providing sufficient disclosure to support a corresponding negative limitation in a claim claiming such alternative embodiment(s), which exclude such very different prior art structure(s)/step(s) way(s).

From reading the present disclosure, other variations and modifications will be apparent to persons skilled in the art. Such variations and modifications may involve equivalent and other features which are already known in the art, and which may be used instead of or in addition to features already described herein.

Although Claims have been formulated in this Application to particular combinations of features, it should be understood that the scope of the disclosure of the present invention also includes any novel feature or any novel combination of features disclosed herein either explicitly or implicitly or any generalization thereof, whether or not it relates to the same invention as presently claimed in any Claim and whether or not it mitigates any or all of the same technical problems as does the present invention.

Features which are described in the context of separate embodiments may also be provided in combination in a single embodiment. Conversely, various features which are, for brevity, described in the context of a single embodiment, may also be provided separately or in any suitable subcombination. The Applicants hereby give notice that new Claims may be formulated to such features and/or combinations of such features during the prosecution of the present Application or of any further Application derived therefrom.

References to "one embodiment," "an embodiment," "example embodiment," "various embodiments," "some embodiments," "embodiments of the invention," etc., may indicate that the embodiment(s) of the invention so described may include a particular feature, structure, or characteristic, but not every possible embodiment of the invention necessarily includes the particular feature, structure, or characteristic. Further, repeated use of the phrase "in one embodiment," or "in an exemplary embodiment," "an embodiment," do not necessarily refer to the same embodiment, although they may. Moreover, any use of phrases like "embodiments" in connection with "the invention" are never meant to characterize that all embodiments of the invention must include the particular feature, structure, or characteristic, and should instead be understood to mean "at least some embodiments of the invention" includes the stated particular feature, structure, or characteristic.

References to "user", or any similar term, as used herein, may mean a human or non-human user thereof. Moreover, "user", or any similar term, as used herein, unless expressly stipulated otherwise, is contemplated to mean users at any stage of the usage process, to include, without limitation, direct user(s), intermediate user(s), indirect user(s), and end user(s). The meaning of "user", or any similar term, as used herein, should not be otherwise inferred or induced by any pattern(s) of description, embodiments, examples, or referenced prior-art that may (or may not) be provided in the present patent.

References to "end user", or any similar term, as used herein, is generally intended to mean late stage user(s) as opposed to early stage user(s). Hence, it is contemplated that there may be a multiplicity of different types of "end user" near the end stage of the usage process. Where applicable, especially with respect to distribution channels of embodiments of the invention comprising consumed retail products/services thereof (as opposed to sellers/vendors or Original Equipment Manufacturers), examples of an "end user" may include, without limitation, a "consumer", "buyer", "customer", "purchaser", "shopper", "enjoyer", "viewer", or individual person or non-human thing benefiting in any way, directly or indirectly, from use of or interaction, with some aspect of the present invention.

In some situations, some embodiments of the present invention may provide beneficial usage to more than one stage or type of usage in the foregoing usage process. In such cases where multiple embodiments targeting various stages of the usage process are described, references to "end user", or any similar term, as used therein, are generally intended to not include the user that is the furthest removed, in the foregoing usage process, from the final user therein of an embodiment of the present invention.

Where applicable, especially with respect to retail distribution channels of embodiments of the invention, intermediate user(s) may include, without limitation, any individual person or non-human thing benefiting in any way, directly or indirectly, from use of, or interaction with, some aspect of the present invention with respect to selling, vending, Original Equipment Manufacturing, marketing, merchandising, distributing, service providing, and the like thereof.

References to "person", "individual", "human", "a party", "animal", "creature", or any similar term, as used herein, even if the context or particular embodiment implies living user, maker, or participant, it should be understood that such characterizations are sole by way of example, and not limitation, in that it is contemplated that any such usage, making, or participation by a living entity in connection with making, using, and/or participating, in any way, with embodiments of the present invention may be substituted by such similar performed by a suitably configured non-living entity, to include, without limitation, automated machines, robots, humanoids, computational systems, information processing systems, artificially intelligent systems, and the like. It is further contemplated that those skilled in the art will readily recognize the practical situations where such living makers, users, and/or participants with embodiments of the present invention may be in whole, or in part, replaced with such non-living makers, users, and/or participants with embodiments of the present invention. Likewise, when those skilled in the art identify such practical situations where such living makers, users, and/or participants with embodiments of the present invention may be in whole, or in part, replaced with such non-living makers, it will be readily apparent in light of the teachings of the present invention how to adapt the described embodiments to be suitable for such non-living makers, users, and/or participants with embodiments of the present invention. Thus, the invention is thus to also cover all such modifications, equivalents, and alternatives falling within the spirit and scope of such adaptations and modifications, at least in part, for such non-living entities.

Headings provided herein are for convenience and are not to be taken as limiting the disclosure in any way.

The enumerated listing of items does not imply that any or all of the items are mutually exclusive, unless expressly specified otherwise.

It is understood that the use of specific component, device and/or parameter names are for example only and not meant to imply any limitations on the invention. The invention may thus be implemented with different nomenclature/terminology utilized to describe the mechanisms/units/structures/components/devices/parameters herein, without limitation. Each term utilized herein is to be given its broadest interpretation given the context in which that term is utilized.

Terminology. The following paragraphs provide definitions and/or context for terms found in this disclosure (including the appended claims):

"Comprising." This term is open-ended. As used in the appended claims, this term does not foreclose additional structure or steps. Consider a claim that recites: "A memory controller comprising a system cache . . . ." Such a claim does not foreclose the memory controller from including additional components (e.g., a memory channel unit, a switch).

"Configured To." Various units, circuits, or other components may be described or claimed as "configured to" perform a task or tasks. In such contexts, "configured to" or "operable for" is used to connote structure by indicating that the mechanisms/units/circuits/components include structure (e.g., circuitry and/or mechanisms) that performs the task or tasks during operation. As such, the mechanisms/unit/circuit/component can be said to be configured to (or be operable) for perform(ing) the task even when the specified mechanisms/unit/circuit/component is not currently operational (e.g., is not on). The mechanisms/units/circuits/components used with the "configured to" or "operable for" language include hardware—for example, mechanisms, structures, electronics, circuits, memory storing program instructions executable to implement the operation, etc. Reciting that a mechanism/unit/circuit/component is "configured to" or "operable for" perform(ing) one or more tasks is expressly intended not to invoke 35 U.S.C. .sctn.112, sixth paragraph, for that mechanism/unit/circuit/component. "Configured to" may also include adapting a manufacturing process to fabricate devices or components that are adapted to implement or perform one or more tasks.

"Based On." As used herein, this term is used to describe one or more factors that affect a determination. This term does not foreclose additional factors that may affect a determination. That is, a determination may be solely based on those factors or based, at least in part, on those factors. Consider the phrase "determine A based on B." While B may be a factor that affects the determination of A, such a phrase does not foreclose the determination of A from also being based on C. In other instances, A may be determined based solely on B.

The terms "a", "an" and "the" mean "one or more", unless expressly specified otherwise.

Unless otherwise indicated, all numbers expressing conditions, concentrations, dimensions, and so forth used in the specification and claims are to be understood as being modified in all instances by the term "about." Accordingly, unless indicated to the contrary, the numerical parameters set forth in the following specification and attached claims are approximations that may vary depending at least upon a specific analytical technique.

The term "comprising," which is synonymous with "including," "containing," or "characterized by" is inclusive or open-ended and does not exclude additional, unrecited elements or method steps. "Comprising" is a term of art used in claim language which means that the named claim elements are essential, but other claim elements may be added and still form a construct within the scope of the claim.

As used herein, the phase "consisting of" excludes any element, step, or ingredient not specified in the claim. When the phrase "consists of" (or variations thereof) appears in a clause of the body of a claim, rather than immediately following the preamble, it limits only the element set forth in that clause; other elements are not excluded from the claim as a whole. As used herein, the phase "consisting essentially of" and "consisting of" limits the scope of a claim to the specified elements or method steps, plus those that do not materially affect the basis and novel characteristic(s) of the claimed subject matter (see *Norian Corp.* v *Stryker Corp.*, 363 F.3d 1321, 1331-32, 70 USPQ2d 1508, Fed. Cir. 2004). Moreover, for any claim of the present invention which claims an embodiment "consisting essentially of" or "consisting of" a certain set of elements of any herein described embodiment it shall be understood as obvious by those skilled in the art that the present invention also covers all possible varying scope variants of any described embodiment(s) that are each exclusively (i.e., "consisting essentially of") functional subsets or functional combination thereof such that each of these plurality of exclusive varying scope variants each consists essentially of any functional subset(s) and/or functional combination(s) of any set of elements of any described embodiment(s) to the exclusion of any others not set forth therein. That is, it is contemplated that it will be obvious to those skilled how to create a multiplicity of alternate embodiments of the present invention that simply consisting essentially of a certain functional combination of elements of any described embodiment(s) to the exclusion of any others not set forth therein, and the invention thus covers all such exclusive embodiments as if they were each described herein.

With respect to the terms "comprising," "consisting of," and "consisting essentially of," where one of these three terms is used herein, the presently disclosed and claimed subject matter may include the use of either of the other two terms. Thus in some embodiments not otherwise explicitly recited, any instance of "comprising" may be replaced by "consisting of" or, alternatively, by "consisting essentially of", and thus, for the purposes of claim support and construction for "consisting of" format claims, such replacements operate to create yet other alternative embodiments "consisting essentially of" only the elements recited in the original "comprising" embodiment to the exclusion of all other elements.

Devices or system modules that are in at least general communication with each other need not be in continuous communication with each other, unless expressly specified otherwise. In addition, devices or system modules that are in at least general communication with each other may communicate directly or indirectly through one or more intermediaries.

A description of an embodiment with several components in communication with each other does not imply that all such components are required. On the contrary a variety of optional components are described to illustrate the wide variety of possible embodiments of the present invention.

As is well known to those skilled in the art many careful considerations and compromises typically must be made when designing for the optimal manufacture of a commercial implementation any system, and in particular, the embodiments of the present invention. A commercial implementation in accordance with the spirit and teachings of the present invention may configured according to the needs of the particular application, whereby any aspect(s), feature(s), function(s), result(s), component(s), approach(es), or step(s) of the teachings related to any described embodiment of the present invention may be suitably omitted, included, adapted, mixed and matched, or improved and/or optimized by those skilled in the art, using their average skills and known techniques, to achieve the desired implementation that addresses the needs of the particular application.

As used herein, "terpene" is a naturally occurring hydrocarbon based on combinations of isoprene units. Terpenoids are compounds related to terpenes, which may include some oxygen functionality or some rearrangement. The two terms may be used interchangeably.

In one embodiment, the invention disclosed herein may include an insect repellent composition. In one embodiment, the insect repellent composition may include at least one terpenoid ester. In another embodiment, the insect repellent composition may include at least one terpenoid ester and at least one terpenoid. In one embodiment, the terpenoid esters may be represented prodrugs capable of undergoing slow hydrolysis after contact with human or animal skin. Accordingly, the composition may be effective as an insect repellent for a prolonged duration.

It may be appreciated by a person with ordinary skill in the art, in light of and in accordance with the teachings of the present invention, that the use of pure terpenes (or terpenoids) may cause skin irritation and/or allergic reactions. Further, they are known to quickly evaporate from the surface of the skin. Accordingly, in one embodiment, are provided terpenoid esters with amino acids, wherein the esters may reduce the side effects of pure terpenoids and may prolong the repellent action of the insect repellent compositions disclosed herein.

In one embodiment, the insect repellent compositions disclosed herein may provide the repellent action in the following manner. After application to a living skin the terpenoid ester may be hydrolyzed to the corresponding terpenoid and organic acid. The initial terpenoids may be released by ester hydrolysis under the action of different esterases, which may be found in the living skin. It may be appreciated by a person with ordinary skill in the art, in light of and in accordance with the teachings of the present invention, that the kinetics of the hydrolysis process may depend on the nature and length of the hydrocarbon radicals in the ester molecule.

It may be appreciated by a person with ordinary skill in the art, in light of and in accordance with the teachings of the present invention, that in one embodiment, the esters compound having a formula I, described hereinbelow, may be prepared by reacting a terpene with an amino acid according to methods known in the art. It is to be understood that the present invention is not limited to any particular method and/or procedure of ester synthesis.

Accordingly, in one embodiment, is provided an ester composition prepared using terpenes and amino acids. The esters may possess insect repellent effects. In one embodiment, is provided insect repellent compositions including the ester compositions.

In one embodiment, is provided a composition having a compound of Formula I:

Formula I

Formula I is an ester of a neurotransmitter amino acid and a terpene, wherein a carboxylic acid group of the amino acid is converted to an ester, and wherein T is a derivative of the terpene and R is a derivative of a neurotransmitter amino acid.

In one embodiment, exemplary terpenoids may include, but are not limited to, monoterpenoids, sesquiterpenoioids, diterpenoids, sesterterpenoids, and triterpenoids. Suitable examples of monoterpenes include, but are not limited to, menthol, carvacrol, thymol, guaiacol, vanillin, eugenol, borneol, camphor, linalool, carvone, α-terpineol, pulegone, eugenol, etc. . . . . Suitable examples of sesquiterpenoids include, but are not limited to, paradisiol, zingiberol, nerolidol, patchoulol and farnesol. Suitable examples of diterpenoids include, but are not limited to, phytol and retinol. Suitable examples of sesterterpenoids include but are not limited to, geranylfarnesol. Suitable examples of triterpenoids include, but are not limited to, cholesterol, cycloartenol, lanosterol, etc.

In various embodiments, the neurotransmitter amino acids used for forming the ester of formula I, may include, but not limited to, GABA, glycine and taurine. In one embodiment, during the synthesis of above stated esters which include an amino acid residue, the esters may be obtained in the basic form (i.e., contain a free amino group) or the form of salt (for example, hydrochloride, hydrobromide, etc.).

It may be appreciated by a person with ordinary skill in the art, in light of and in accordance with the teachings of the present invention, that the administration of the ester composition including compound having Formula I may be performed by any means and methods that may be used to administer the compounds possessing insect repellent effects. Suitable methods of administration include, but are not limited to topical application. It may be appreciated by a person with ordinary skill in the art, in light of and in accordance with the teachings of the present invention, that topical method may have advantages including, but not limited to, direct action and, consequently, reduction of systematic side-effects for topical route. It may be appreciated by a person with ordinary skill in the art, in light of and in accordance with the teachings of the present invention, that the following dosage forms may be applied to deliver the ester composition including the formula I, for example, in the form of creams, ointments, gels, lotions, pastes, solutions, etc. . . . .

In one embodiment, the ester composition including compound having formula I may be formulated for topical administration in combination with any pharmaceutically acceptable compound. It may be appreciated by a person with ordinary skill in the art, in light of and in accordance with the teachings of the present invention, that the following dosage forms may be applied to deliver the ester composition including the formula I, for example, in the form of ointments, gels, lotions, pastes, solutions, etc. . . . In an exemplary embodiment, the ointment preparation may include, but not be limited to, lanolin, petrolatum, paraffin, polyethylene glycol, stearic acid, carnauba wax, cetyl alcohol, emulsifying wax, hydrogenated castor oil, etc.

In certain embodiments, the insect repellent composition disclosed herein may be administered using methods, including, but not limited to, patches, powder (with or without excipients), repellent tablets, etc. In one embodiment, when the composition is administered as a patch, application of double-layer drug-in adhesive patch with controlled drug delivery may be considered. In one embodiment, the structure of the patch may include two separated reservoirs: the first one is an outer reservoir and may include free terpenes or terpenoids and the second one is an inner reservoir and may include terpenoid esters. It may be appreciated by a person with ordinary skill in the art, in light of and in accordance with the teachings of the present invention, that free terpenes are known to cause skin irritation, therefore, the first reservoir may not be in contact with skin, while the terpenoid esters are known not to cause skin irritation and thus the second reservoir may come in contact with the human or animal skin. These double-layer drug-in adhesive patches may allow controlling the release rate of terpenoids esters depending on the content of the compositions. In various embodiments, any device (for example, fumigator, etc.) or processes (for example, heating, etc . . . ) aimed at expression and/or enhancement of a repellent action of the terpenoid esters may be employed in the administration/delivery mode of the insect repellent compositions disclosed herein.

In various embodiments, compositions consisting of the abovementioned esters in different combinations and ratios are also provided. In one embodiment, the amount of ester composition including compound having formula I in a topical composition may be in a range of from about 0.5 percent to about 30 percent weight by weight based on a total weight of the topical composition.

In one embodiment, an insect repellent composition including the ester compound having formula I and a pharmaceutically acceptable base may be provided. In one embodiment, the amount of ester composition including compound having formula I in a topical composition may be in a range of from about 0.5 percent to about 30 percent weight by weight based on a total weight of the topical composition. In one embodiment, the amount of pharmaceutically acceptable base in the topical composition may be in a range of from about 70 percent to about 99.5 percent weight by weight based on a total weight of the topical composition.

In one embodiment, an insect repellent composition including the ester compound having formula I, a terpenoid, and a pharmaceutically acceptable base may be provided. In one embodiment, the amount of compound having formula I in a topical composition may be in a range of from about 0.5 percent to about 30 percent weight by weight based on a total weight of the topical composition. In one embodiment, the amount of terpenoid in a topical composition may be in a range of from about 0.5 percent to about 10 percent weight by weight based on a total weight of the topical composition. In one embodiment, the amount of pharmaceutically acceptable base in the topical composition may be in a range of from about 60 percent to about 99 percent weight by weight based on a total weight of the topical composition.

In one embodiment, the composition includes an alcohol-free insect repelling composition, comprising: terpene ester in an amount in a range of from about 0.5 weight percent to about 30 weight percent and inactive base in an amount in a range of about 70 weight percent to about 99.5 weight percent based on the weight of the composition. In another embodiment, the composition includes an alcohol-free insect repelling composition, comprising: terpene ester in an amount in a range of from about 0.5 weight percent to about 20 weight percent; terpene in an amount in a range of from about 0.5 weight percent to about 10 weight percent and inactive base in an amount in a range of about 70 weight percent to about 99 weight percent based on the weight of the composition. The United States Environmental Protection Agency has registered citronella EO (essential oil), eucalyptus EO and other plant oils as safe and effective ingredients for use as topical insect repellents. However, caution is recommended in the use of EOs in general due to a number of potential toxic effects and the allergenicity of EO chemical components. These effects are associated with multi-component composition of essential oils, which limits their use.

In one embodiment, the insect repelling composition disclosed herein may include various advantages, including, but not limited to, 1) the compositions comprises esters based on the substances of natural origin; 2) is effective in repelling insects of various types; 3) the terpenoid esters may be hydrolyzed to the starting terpenoids in the human and/or animal skin under the action of enzymatic systems with a gradual release of the active ingredients, thus demonstrating/providing prolonged repellent activity; 4) the absence of unpleasant odor inherent to compositions with synthetic repellents; 5) may be environmentally safe and may also be used on domesticated animals and horses; 6) may be applied to human skin with no/minimum known adverse effects; 7) they can also be used on animals which is an inexpensive way to prevent diseases and infection in livestock and house pets; 8) eliminate undesired agents (as terpenes are the part of more complex substances in nature), and the like.

It may be appreciated by a person with ordinary skill in the art, in light of and in accordance with the teachings of the present invention, that use of the ester compositions having compound of formula I of the present invention includes but is not limited to repel mosquitoes, flies, ticks, fleas, and other biting insects.

EXPERIMENTAL SECTION

Example 1

A composition for topical administration containing a compound of formula 1.

The composition is prepared by combining the following ingredients:

Thymol GABA ester (5 weight percent, 5 grams (g)), inactive base (95 weight percent, 95 g)

The resultant cream, was applied on clean human or animal skin. After a duration of about 15 to 20 minutes after application, the ester present in the cream undergoes enzymatic degradation leading to release of pure terpenoid via a hydrolysis process. The beginning of the hydrolysis process is determined organoleptically based on detection of a pleasant terpenoid odor. The repellent activity continued for a period of about 9 to 12 hours.

Example 2

A composition for topical administration containing a compound of formula 1.

The composition is prepared by combining the following ingredients:

Thymol (2 weight percent, 2 g), Thymol GABA ester (5 weight percent, 5 g, inactive base (93 weight percent, 93 g).

The resultant cream, was applied on clean human or animal. As the product contains thymol in free form its repellent activity occurred immediately after application. After a duration of about 15 to 20 minutes after application, the ester present in the cream undergoes enzymatic degradation leading to release of pure thymol via a hydrolysis process to provide a prolonged repellent activity that continued for a period of about 9 to 12 hours.

Example 3

A composition for topical administration containing a compound of formula 1.

The composition is prepared by combining the following ingredients:

Vanillin (2 weight percent, 2 g), borneol (2 weight percent, 2 g), borneol GABA ester (2 weight percent, 2 g), vanillin GABA ester (2 weight percent, 2 g), and inactive base (92 weight percent, 92 g)

The resultant cream, was applied on clean human or animal. As the product contains vanillin and borneol in free form its repellent activity occurred immediately after application. After a duration of about 15 to 20 minutes after application, the ester present in the cream undergoes enzymatic degradation leading to release of pure vanillin via a hydrolysis process to provide a prolonged repellent activity that continued for a period of about 9 to 12 hours.

Example 4

A composition for topical administration containing a compound of formula 1.

The composition is prepared by combining the following ingredients:

Carvacrol (2 weight percent, 2 g), Carvacrol-GABA ester (2 weight percent, 2 g), and inactive base (96 weight percent, 96 g)

The resultant cream, was applied on clean human or animal. As the product contains carvacrol in free form its repellent activity occurred immediately after application. After a duration of about 15 to 20 minutes after application, the ester present in the cream undergoes enzymatic degradation leading to release of pure carvacrol via a hydrolysis process to provide a prolonged repellent activity that continued for a period of about 9 to 12 hours.

Those skilled in the art will readily recognize, in light of and in accordance with the teachings of the present invention, that any of the foregoing steps may be suitably replaced, reordered, removed and additional steps may be inserted depending upon the needs of the particular application. Moreover, the prescribed method steps of the foregoing embodiments may be implemented using any physical and/or hardware system that those skilled in the art will readily know is suitable in light of the foregoing teachings. For any method steps described in the present application that can be carried out on a computing machine, a typical computer system can, when appropriately configured or designed, serve as a computer system in which those aspects of the invention may be embodied. Thus, the present invention is not limited to any particular tangible means of implementation.

All the features disclosed in this specification, including any accompanying abstract and drawings, may be replaced by alternative features serving the same, equivalent or similar purpose, unless expressly stated otherwise. Thus, unless expressly stated otherwise, each feature disclosed is one example only of a generic series of equivalent or similar features.

It is noted that according to USA law 35 USC § 112 (1), all claims must be supported by sufficient disclosure in the present patent specification, and any material known to those skilled in the art need not be explicitly disclosed. However, 35 USC § 112 (6) requires that structures corresponding to functional limitations interpreted under 35 USC § 112 (6) must be explicitly disclosed in the patent specification. Moreover, the USPTO's Examination policy of initially treating and searching prior art under the broadest interpretation of a "mean for" claim limitation implies that the broadest initial search on 112(6) functional limitation would have to be conducted to support a legally valid Examination on that USPTO policy for broadest interpretation of "mean for" claims. Accordingly, the USPTO will have discovered a multiplicity of prior art documents including disclosure of specific structures and elements which are suitable to act as corresponding structures to satisfy all functional limitations in the below claims that are interpreted under 35 USC § 112 (6) when such corresponding structures are not explicitly disclosed in the foregoing patent specification. Therefore, for any invention element(s)/structure(s) corresponding to functional claim limitation(s), in the below claims interpreted under 35 USC § 112 (6), which is/are not explicitly disclosed in the foregoing patent specification, yet do exist in the patent and/or non-patent documents found during the course of USPTO searching, Applicant(s) incorporate all such functionally corresponding structures and related enabling material herein by reference for the purpose of providing explicit structures that implement the functional means claimed. Applicant(s) request(s) that fact finders during any claims construction proceedings and/or examination of patent allowability properly identify and incorporate only the portions of each of these documents discovered during the broadest interpretation search of 35 USC § 112 (6) limitation, which exist in at least one of the patent and/or non-patent documents found during the course of normal USPTO searching and or supplied to the USPTO during prosecution. Applicant(s) also incorporate by reference the bibliographic citation information to identify all such documents comprising functionally corresponding structures and related enabling material as listed in any PTO Form-892 or likewise any information disclosure statements (IDS) entered into the present patent application by the USPTO or Applicant(s) or any $3^{rd}$ parties. Applicant(s) also reserve its right to later amend the present application to explicitly include citations to such documents and/or explicitly include the functionally corresponding structures which were incorporate by reference above.

Thus, for any invention element(s)/structure(s) corresponding to functional claim limitation(s), in the below claims, that are interpreted under 35 USC § 112 (6), which is/are not explicitly disclosed in the foregoing patent specification, Applicant(s) have explicitly prescribed which documents and material to include the otherwise missing disclosure, and have prescribed exactly which portions of such patent and/or non-patent documents should be incorporated by such reference for the purpose of satisfying the disclosure requirements of 35 USC § 112 (6). Applicant(s) note that all the identified documents above which are incorporated by reference to satisfy 35 USC § 112 (6) necessarily have a filing and/or publication date prior to that of the instant application, and thus are valid prior documents to incorporated by reference in the instant application.

Having fully described at least one embodiment of the present invention, other equivalent or alternative ester compositions having a compound of formula I and methods of preparing the same according to the present invention will be apparent to those skilled in the art. Various aspects of the invention have been described above by way of illustration, and the specific embodiments disclosed are not intended to limit the invention to the particular forms disclosed. The particular implementation of the ester compositions having a compound of formula I and methods of preparing the same may vary depending upon the particular context or application. By way of example, and not limitation, the ester compositions having a compound of formula I and methods of preparing the same described in the foregoing were principally directed to analgesic and anti-inflammatory implementations; however, similar techniques may instead be applied to which implementations of the present invention are contemplated as within the scope of the present invention. The invention is thus to cover all modifications, equivalents, and alternatives falling within the spirit and scope of the following claims. It is to be further understood that not all of the disclosed embodiments in the foregoing specification will necessarily satisfy or achieve each of the objects, advantages, or improvements described in the foregoing specification.

Claim elements and steps herein may have been numbered and/or lettered solely as an aid in readability and understanding. Any such numbering and lettering in itself is not intended to and should not be taken to indicate the ordering of elements and/or steps in the claims.

The corresponding structures, materials, acts, and equivalents of all means or step plus function elements in the claims below are intended to include any structure, material, or act for performing the function in combination with other claimed elements as specifically claimed.

The corresponding structures, materials, acts, and equivalents of all means or step plus function elements in the claims below are intended to include any structure, material, or act for performing the function in combination with other claimed elements as specifically claimed. The description of the present invention has been presented for purposes of illustration and description, but is not intended to be exhaustive or limited to the invention in the form disclosed. Many modifications and variations will be apparent to those of ordinary skill in the art without departing from the scope and spirit of the invention. The embodiment was chosen and described in order to best explain the principles of the invention and the practical application, and to enable others of ordinary skill in the art to understand the invention for various embodiments with various modifications as are suited to the particular use contemplated.

The Abstract is provided to comply with 37 C.F.R. Section 1.72(b) requiring an abstract that will allow the reader to ascertain the nature and gist of the technical disclosure. That is, the Abstract is provided merely to introduce certain concepts and not to identify any key or essential features of the claimed subject matter. It is submitted with the understanding that it will not be used to limit or interpret the scope or meaning of the claims.

The following claims are hereby incorporated into the detailed description, with each claim standing on its own as a separate embodiment.

The invention claimed is:

1. A composition comprising:
   a compound having a formula I:

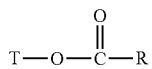

I wherein T is terpenoid and R is a neurotransmitter amino acid, wherein the neurotransmitter amino acids are selected form GABA, glycine, and taurine;
   wherein the compound of formula I is present in an amount in a range of from about 0.5 weight percent to about 30 weight percent based on the weight of the composition;
   a pharmaceutically acceptable base, wherein the pharmaceutically acceptable base is present in an amount in a range of from about 70 percent to about 99.5 percent based on the weight of the composition.

2. The composition of claim 1, comprising a monoterpenoid in an amount in a range of from about 0.5 weight percent to about 10 weight percent based on the weight of the composition.

3. The composition of claim 1, wherein the composition is delivered in the form of an ointment, a gel, a lotion, a solution, or a spray.

4. The composition of claim 1, wherein terpenoid ester is derived from carvacrol and gamma-aminobutyric acid

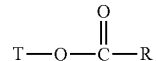

wherein T is carvacrol and R is GABA

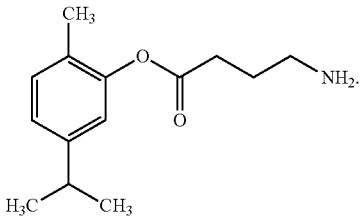 [SMILES: Cc1ccc(C(C)C)cc1OC(=O)CCCN]

5. The composition of claim 4, further comprising from about 0.5 to about 10 weight percent of carvacrol based on a total weight of composition.

6. The composition of claim 2, wherein the composition is delivered in the form of an ointment, a gel, a lotion, a solution, or a spray.

* * * * *